United States Patent [19]

Neumeier et al.

[11] Patent Number: 5,302,370
[45] Date of Patent: Apr. 12, 1994

[54] CHELATING AGENTS FOR FORMING COMPLEXES WITH RADIOACTIVE ISOTOPES, METAL COMPLEXES THEREOF AND USE THEREOF IN DIAGNOSIS AND THERAPY

[75] Inventors: Reinhard Neumeier; Wolfgang Kramp, both of Berlin; Helmut R. Mäcke, Lorrach, all of Fed. Rep. of Germany

[73] Assignee: Institut fur Diagnostikforschung GmbH, Berlin, Fed. Rep. of Germany

[21] Appl. No.: 572,140

[22] Filed: Aug. 22, 1990

[30] Foreign Application Priority Data

Sep. 11, 1989 [DE] Fed. Rep. of Germany ....... 3930674

[51] Int. Cl.⁵ .................. A61K 49/02; C07C 211/27; C07C 211/25
[52] U.S. Cl. .................. 424/1.53; 424/1.65; 534/10; 534/14; 530/391.5; 548/518; 548/546; 548/561; 564/367; 564/370; 564/336; 564/337; 564/310; 564/313; 564/464; 549/59; 549/74; 549/75
[58] Field of Search .............. 424/1.1, 9; 534/10, 534/14; 530/391.5; 548/518, 561, 546; 564/370, 367, 361, 355, 336, 310, 337, 313, 464; 549/59, 74, 75

[56] References Cited

U.S. PATENT DOCUMENTS

| | | | |
|---|---|---|---|
| 2,624,759 | 1/1953 | Bersworth | 564/367 X |
| 2,876,236 | 3/1959 | Szabo et al. | 549/59 |
| 3,933,913 | 1/1976 | Colella et al. | 564/367 |
| 4,152,345 | 5/1979 | Gaudette et al. | 564/367 X |
| 4,758,682 | 7/1988 | Collins et al. | 534/14 |
| 5,071,965 | 12/1991 | Dunn et al. | 534/14 |
| 5,101,041 | 3/1992 | Troutner et al. | 548/518 |
| 5,104,638 | 4/1992 | Nosco | 424/1.1 |

*Primary Examiner*—Robert L. Stoll
*Assistant Examiner*—John M. Covert
*Attorney, Agent, or Firm*—Millen, White, Zelano & Branigan

[57] ABSTRACT

The invention relates to compounds having the general formula I

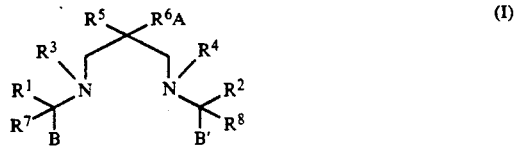

where A if required can contain a functional and/or activated group C for coupling to selectively concentrating compounds or can contain a selectively concentrating compound coupled via the group C. B and B' are functional groups for coordinate bonding of groups carrying metal ions. The novel compounds are for forming complexes with radioactive metal ions, more particularly rhenium and technetium isotopes, and are used in medical diagnosis and therapy.

8 Claims, No Drawings

CHELATING AGENTS FOR FORMING COMPLEXES WITH RADIOACTIVE ISOTOPES, METAL COMPLEXES THEREOF AND USE THEREOF IN DIAGNOSIS AND THERAPY

Radioactive metal ions, usually bonded to a complexing agent, have long been used for in-vivo diagnosis. Among these, the radionuclide most frequently used in clinical nuclear medicine is technetium-99 m (Tc-99 m) because of its almost ideal physical properties for these purposes—i.e. good absorption of radiation in appropriate detection devices (gamma cameras, SPECT apparatus) in contrast to low absorption in the human organism and ready availability via a molybdenum-technetium generator. Its short half-life of 6.02 h guarantees that the patient is only slightly subjected to gamma radiation, particularly since the daughter nuclide technetium-99 has negligible residual radioactivity. Its disadvantage, however, is its complex-chemistry, which is complicated and not yet fully understood. Technetium can occur in a number of oxidation stages ($+7$ to $-1$), which can greatly change the pharmacological properties through changing the charge of a complex. It is therefore necessary to synthesise complexes which bond technetium in a defined oxidation stage and prevent redox reactions which could result in redistribution of the drug. A number of such Tc-99 m complexing agents are already known and used in treatment. Neutral complexes are frequently systems in which Tc-99 m is bonded between 2-4 nitrogen atoms and 0-2 sulphur atoms ($N_2S_2$, —$N_3S$— and proplylene amine oxime complexes). Often however the inadequate stability of these Tc-99 m complexes is a serious disadvantage (Hung, JC. et al.; J. Nucl. Med. 29: 1568, 1988). In clinical use, it is necessary e.g. to apply HMPAO (hexamethyl propylene amine oxime) shortly after labelling with pertechnetate, to prevent excessive increase in the proportion of decomposition products which reduce the accuracy of diagnosis. These chelates or chelating agents cannot be coupled to other substances which selectively accumulate in foci of disease. Consequently most of the aforementioned complexes are distributed in a manner depending on the circulation and/or metabolic activity of an organ (e.g. EPA 0 194 843), so that necrotic or ischaemic regions, e.g. after an infarction or stroke, can be shown in a scintigram.

However, substances representing molecular changes in the diseased tissue are much more promising for successful diagnosis of tumours, neurological diseases or diseases of the heart and circulation, since they become specifically bonded to the diseased tissue or become incorporated in the metabolism. As a result of biological and biochemical basic research, it is possible to select a number of substances which become selectively concentrated in foci of disease. Some tumours develop increased or reduced surface concentrations on receptors, e.g. for growth factors or steroid hormones (Sledge, G. W.; Adv. Cancer Res. 38: 61-75 [1983]). In neurological diseases also there is a change in concentration of receptors for neurotransmitters in certain regions of the brain (Frost, J. J.; Trends Pharmacol. Sci. 7: 490-496 [1987]). Also, diseased or injured cells or cells transformed to tumour cells often show considerable changes in their metabolism and a deficiency of oxygen in the tumour. These physiological peculiarities can be used in in-vivo diagnosis, e.g. by coupling hormones, growth factors, neurotransmitters or certain metabolic products such as fatty acids, saccharides, peptides or amino acids to chelating agents for Tc-99m. Substances such as misonidazole (a radiosensitiser) or other compounds which are converted to radicals in the absence of oxygen can also be used for specific concentration of radioactive isotopes, resulting in pictorial representation of tumours or ischaemic regions. A final possibility is coupling to monoclonal antibodies which have become a very promising instrument in tumour diagnosis owning to their specificity.

In order to provide diagnostics in the manner described it is necessary to couple chelating agents for radioactive metal ions, more particularly Tc-99m, to substances which become selectively concentrated in diseased tissue.

Since the isotopes of rhenium (Re-188 and Re-186) have similar chemical properties to Tc-99m, chelating agents can also be used for complexing the latter isotopes. The aforementioned Re-isotopes are beta emitters. Accordingly the selectively concentrating substances can also be used in tumor therapy when complexed with rhenium instead of technetium.

Previous attempts to couple chelating agents to selectively concentrating substances are unsatisfactory for many reasons. If the functional groups of the complexing agents are used for bonding the chelating agent to such a molecule the result frequently is a weakening of the stability of the complex, i.e. the proportion of the isotope released from the conjugate is greater than that which can be tolerated in diagnosis. (Brechbiel, M. W. et. al., Inorg. Chem. 25:2772 [1986]). It is therefore necessary to produce bifunctional complexing agents, i.e. complexing agents which contain functional groups for coordinate bonding of the desired metal ion and also contain one (other) functional group for bonding the selectively concentrating molecule. These bifunctional ligands can be used for specific chemically-defined bonding of technetium to a wide variety of biological materials, even when "pre-labelling" is carried out. In this method, labelling with Tc-99m and isolation of the complexes both precede a second step in which the complex is linked to a selectively concentrating molecule, with the result that the labelled compounds are obtained with high purity.

There are descriptions of some chelating agents coupled to monoclonal antibodies (e.g. EPA 0 247 866 and EPA 0 188 256) or fatty acids (EPA 0 200 492). The chelating agents used, however, are the previously-mentioned $N_2S_2$ systems which are unsuitable owing to their low stability. The somewhat more stable $N_3S$ chelates, when coupled to monocional antibodies, do not lose so much Tc-99m from the conjugates (J. Lister-James; J. Nucl. Med. 30:793 and EPA 0 284 071).

Since there are wide differences both in the properties of the selectively concentrating substances and in the mechanisms by means of which they concentrate, it is also necessary to vary the chelating agents capable of coupling and to be able to adapt the physiological requirements of the coupling reactant with regard to lipophilic and hydrophilic properties and permeability or impermeability through membranes, etc.

For these reasons there is an urgent need for stable complex compounds which are coupled or capable of being coupled to various selectively concentrating compounds.

The object of the invention therefore is to provide stable chelating agents containing a functional group for coupling to a selectively concentrating compound or containing a selectively concentrating compound coupled by means of this functional group.

According to the invention this problem is solved by compounds having the general formula I

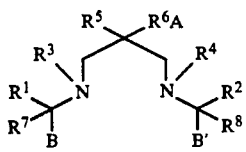 (I)

where $R^1$, $R^2$ and $R^5$ are the same or different and stand for hydrogen or a $C_{1-6}$-alkyl radical, substituted if required by a hydroxyl group, $R^3$ and $R^4$ are the same or different and stand for a hydrogen atom or $C_{1-6}$-alkyl or amino($C_{1-6}$)-alkyl or carboxymethyl or ($C_{1-5}$-alkoxycarbonyl)methyl or ($C_{1-6}$-alkoxycarbonyl)benzyl radical, $R^6$ stands for a $C_{1-6}$-alkylene radical, $R^7$ and $R^8$ are the same or different and stand for hydrogen or a $C_{1-5}$-alkyl radical and B and B' are the same or different and stand for a phenyl or naphthyl or 2-mercaptophenyl or thienyl or pyrrolyl or nitrosomethyl radical, substituted with 1–3 hydroxyl groups and having the formula $$\begin{array}{c} NO \\ | \\ -CH \\ | \\ R^x \end{array}$$

where $R^x$ denotes a $C_{1-6}$-alkyl radical which, together if required with $R^1$ or $R^2$, is cyclised via a trimethylene or tetramethylene group to form a 5 or 6 ring, and A denotes a functional group C, where C stands for an amino or hydrazino or hydrazido or carboxy or $C_{2-6}$-alkinyl or alkenyl or hydroxyl or aminophenyl or oxiranyl or fluorinated phenoxycarbonyl or halogen or formyl or nitrile or phenylisothiocyanate or a succinimide oxycarbonyl radical which latter is substituted if required with a sodium sulphate radical, or contains a compound T bonded by means of the functional group C and selectively concentrating in lesions or certain tissues, where T stands for monoclonal antibodies or fragments thereof or hormones or enzymes or growth factors or ligands for cell membrane receptors or steroids or neurotransmitters or lipids or saccharides or aminoacids or oligopeptides or biotin or radiosensitizers such as misonidazola, and complexes thereof with radioactive metal ions suitable for diagnosis and tumor therapy, and salts thereof with inorganic and organic acids.

According to the invention, preference is given to those compounds according to claim 1 in which $R^1$, $R^2$, $R^7$ and $R^8$ are hydrogen atoms or methyl radicals or those compounds according to claim 1 in which the functional group C, if present in A, stands for a carboxyl or amino or $C_{2-5}$-alkenyl or $C_{2-5}$-alkinyl, or nitrile or tetrahydropyranyloxy or nitrophenyl or oxiranyl or aminophenyl or phenylisothiocyanate radical and the selectively concentrating compound T if present in A stands for monoclonal antibodies, fragments thereof, biotin or misonidazole.

Surprisingly, many of the synthesised chelates labelled with Tc-99m have higher stability than the comparable $N_2S_2$—, $N_3S$— and propylene amine oxime chelates. In the case for example of one substance according to the invention (example 12) coupled to biotin via an aminophenyl radical, no decomposition products were observed after 5 hours, in contrast to the case of HMPAO, a comparable substance known from the literature (Hung, J. C. et al.; J. Nucl. Med. 29: 1568, 1988). It has also been shown by competition tests that the Tc-99m chelates described according to the invention form complexes better than the comparable $N_2S_2$—, $N_3S$— and propylene amine oxime chelates. The chelates described according to the invention are therefore appreciably more suitable for diagnostic and therapeutic purposes than the previously-mentioned chelates.

To prepare the compounds according to claim 1 a 1,3-propane diamine having the general formula II

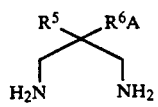 (II)

where $R^5$, $R^6$ and A have the meanings given previously, is reacted with a compound having the general formula III or IV

 B—$R^1$C=O (III)

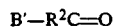 B'—$R^2$C=O (IV), in which $R^1=R^2$, B=B' and $R^1,R^2$,B and B' have the meanings given previously, in a polar solvent, preferably ethanol, or by using a water separator in a non-polar solvent, preferably benzene, at temperatures of 25°–180° C. within 6 hours and 3 days, the amino group is reduced in known manner, preferably with sodium boron hydride in a polar solvent, preferably a methanol-water mixture, at temperatures of 25°–100° C. within 0.5 to 24 hours preferably 2 days, or a propane diamine having the general formula II

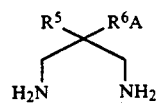 (II)

in which $R^5$, $R^6$ and A have the meanings given previously, is reacted with a compound having the general formula V or VI

 B—CO—X (V)

 B'—CO—X (VI), in which B=B' and B and B' have the meanings given previously, the hydroxyl, mercapto and amino groups in B are in protected form and X stands for a halogen atom, preferably a chlorine atom, or substituted malonic acid halides, preferably malonic acid chlorides having the general formula VII,

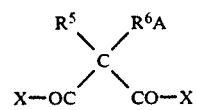 (VII)

in which $R^5$ and $R^6$ have the meanings given previously, X stands for a halogen atom and any hydroxyl groups in B are present in protected form, is reacted with an amine having the general formula VIII or IX

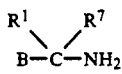  (VIII)

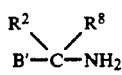  (XI)

in which $R^1=R^2$, $R^7=R^8$, $B=B^1$ and $R^1$, $R^2$, $R^7$, $R^8$, B and B' have the meanings given previously, in an aprotic solvent, preferably dichloromethane, at temperatures of 0°–180°, preferably at room temperature, for 2 to 24 hours, preferably 4 hours with addition of triethylamine, the amide group is reduced in known manner to the corresponding amino group, preferably with borane in THF or lithium aluminium hydride in an aprotic solvent, preferably diethylether, at temperatures of 25°–150° C. in 0.5 to 24 hours, preferably 8 hours, If desired, the amino groups can be conventionally reacted, after the reactions described above, to add thereto the groups $R^4$ and/or $R^4$, as defined above, in a known manner; also, if desired, any protected groups are split off, and the compounds obtained in these equivalent ways, if required before generating the free functional group C at the amino groups are protected with protective ions, e.g. in the form of a Cu complex, and, if required, the resulting compounds are subsequently coupled via the functional group C in A to selectively concentrating T compounds and, if required, the aromatic substituents B and B' are formed into complexes with the required radioactive isotope, and any protective ions previously present in the product are removed by methods known in the literature and the sequence of the steps of complex-forming with technetium or rhenium isotopes and coupling T can be changed over.

The hydroxy protective groups can e.g. be the benzyl or 4-methoxybenzyl or 4-nitrobenzyl or trityl or diphenylmethyl or trimethylsilyl or dimethyl-t-butylsilyl or diphenyl-t-butylsilyl group. In the case of polyols, the hydroxy groups can also be protected in the form of ketals, e.g. with acetone, acetaldehyde, cyclohexanone or benzaldehyde. The hydroxy groups can also occur e.g. as THP-ethers or α-alkoxyethyl ethers or MEM ethers or esters of aromatic or aliphatic carboxylic acids, e.g. acetic acid or benzoic acid. The hydroxy protective groups can be liberated by methods known to the skilled addressee, e.g. by hydrogenolysis, reductive splitting with lithium and ammonia, treatment of ethers and ketals with acid or alkali treatment of esters (see e.g. "Protective Groups in Organic Synthesis", T. W. Green, John Wiley and Sons 1981).

The amino protective groups can e.g. be trifluoroacetyl or .t-butoxycarbonyl or 2,2,2-trichloroethoxycarbonyl or benzoxycarbonyl or acetyl groups. The amino protective groups can be split off by methods known in the literature, e.g. by basic or acid hydrolysis, reductive splitting with zinc in acetic acid, or hydrogenolysis.

The mercapto protective groups can be $C_{1-5}$ alkyl radicals or benzylthio ethers. The mercapto protective groups are optionally split off by alkali-metal alkyl thiolates, alkali-metal alcoholates or alkali metals, preferably with sodium methyl thiolate in a polar solvent, preferably in HMPT, DMF or dimethyl acetamide or by reductive splitting with sodium and ammonia.

Non-symmetrical compounds (B≠B') can be prepared by using commercially available mixed malonic acid esters which initially enable only one of the two different ester groups to be selectively converted to the carboxylic acid amide. These substances may more particularly be methyl, benzyl or t-butylesters, which can easily be selectively saponified by methods known in the literature, together with other carboxylic acid esters, e.g., an ethyl ester. The resulting free carboxylic acid group is converted in known manner to the corresponding carboxylic acid chloride and then reacted with a primary amine, substituted if required, to give a secondary carboxylic acid amide. The remaining ester group is then reacted as described with ammonia to form a primary carboxylic acid amide and then the two different acid amide groups are reduced in known manner to the differently substituted amines.

As already described, the primary amino group can be reacted with a compound of formula III or IV to form the corresponding imine. The remaining secondary amino group can then be reacted with a formula III or IV compound in known manner under reductive alkylation conditions, the imino group being simultaneously reduced to the amine.

The radical C is suitable for producing a stable bond to proteins or other selectively concentrating molecules. If the functional group C is suitably chosen, coupling can occur under gentle reaction conditions which do not influence the biological function and/or selectivity.

Coupling to the desired compounds is also brought about by known methods (e.g. Fritzberg et al.; J. Nucl. Med.: 26,7 [1987]), e.g. by reacting the group C with nucleophilic groups of the selectively concentrating molecule or, if the group C is itself nucleophilic, with activated groups of the selectively concentrating molecule.

The group C represents any substitient which is a functional group which can bring about coupling to a selectively concentrating molecule under gentle conditions (e.g. by acylation or amidation) or any activated group which can react with nucleophilic groups of proteins, antibodies, hormones or other bio-molecules e.g. the amino or phenol or sulfhydryis or formyl or imidazole group. "Activitated group" means a group capable of forming a conjugate and reacting with a nucleophilic substituent of a selectively concentrating molecule or of the complex ligand itself in aqueous solution within a reasonable short time and under reaction conditions which do not denature or destroy the biological activity. Examples of such substances are imido-esters, alkylimido-esters, amidoalkylimido-esters, succinimido-esters, acylsuccinimides, phenolic esters, substituted phenolic esters, tetrafluorophenolic esters, anhydrides, hydrazides, alkyl halides and Michael acceptors. C is preferably a monoanhydride or acid chloride or acid hydrazide or mixed anhydride or activated ester (such as phenolic or imido-ester) or nitren or isothiocyanate, more particularly for coupling with nucleophilic groups of amino acids, or an aliphatic or aromatic primary amine for coupling to carbohydrate radicals of proteins.

If the group C is itself nucleophilic, it can react with activated groups of a selectively concentrating molecule, including groups of the molecule reacting with cross-linking reagents, such as homobifunctional imido esters, homobifunctional N-hydroxysuccininido esters (NHS) and heterobifunctional cross-linkers containing various functional groups such as NHS esters, pyridyl disulphides and activated halogens such as α-ketohalides. These cross-linkers are commercially obtainable.

The coupling reactants (=compound T) can be various bio-molecules, such as ligands which bond to specific receptors and can thus recognise a tissue where the receptor density has changed. These substances include peptide and steroid hormones, growth factors and neurotransmitters. It has been shown that diagnosis of breast and prostate carcinoma can be improved by using ligands for steroid hormone receptors (S. J. Brandes and J. A. Kaztzenellenbogen, Nucl. Med. Biol. 15:53, 1988). Tumour cells have different changes in density of receptors for peptide hormones or growth factors such as the epidermal growth factor (EGF). The differences in concentration can be used for selective enrichment of cytostatics in tumour cells (E. Aboud-Pirak et al., Proc. Natl. Acad. Sci. USA 86: 3778, 1989). Ligands for neuroreceptors and labelled with positron-emitting isotopes can often be used for diagnosis of various brain diseases (J. J. Forst, Trends in Phazrmacol. Sci. 7: 490, 1987). However, bio-molecules are metabolites which can be inserted into the metabolism of cells and show a change in the metabollism. These substances include fatty acids, saccharides, peptides and amino acids. Fatty acids coupled to the relatively unstable $N_2S_2$ chelating agents have been described in EPA 0 200 492. Other metabolic products such as saccharides (deoxyglucose), lactate, pyruvate and amino acids (leucine, methyl methionine and glycine) have been used in the PET technique for pictorial representation of changed metabolic processes (R. Weinreich, Swiss Med.; 8.10.1986). Non-biological substances such as misonidazole and derivatives thereof which become irreversibly bonded to cell constituents in tissues or parts of tissues with reduced oxygen concentration can also be used for specific concentration of radioactive isotopes and consequent pictorial representation of tumours or ischaemic regions (M. E. Shelton, J. Nucl. Med. 30: 351, 1989). Finally, bifunctional chelating agents can also be coupled to monoclonal antibodies or fragments thereof. The biotin-containing compounds according to the invention can be used for bonding radioactive conjugates to substances containing avidin or streptavidin. This can be used to increase the concentration of antibody-streptavidin conjugates in the tumour before applying the radioactive biotin-containing component, thus reducing the exposure of the patient to radiation (D. J. Hnatowich et al., J. Nucl. Med. 28: 1294, 1987). Conjugates can be complexed with Tc-99m or rhenium isotopes for the purpose of diagnosis and treatment of tumours.

It does not matter whether the chelating agent is labelled with Tc-99m or a rhenium isotope before or after coupling to the selectively concentrating molecule. However, if coupling to the selectively concentrating molecule occurs after forming a complex, the reaction between the radioactive complex and the concentrating compound must occur quickly, under gentle conditions and almost quantitatively, and no subsequent purification must be necessary.

The pharmaceutical agents according to the invention are prepared in known manner, in that the complexing agents according to the invention are dissolved in an aqueous medium, adding a reducing agent, preferably tin (II) salts such as the chloride or tartrate together with conventional galenic additives if required, followed by sterile filtration. The additives may e.g. be physiologically compatible buffers (e.g. tromethamine) or small amounts of electrolytes (e.g. sodium chloride) or stabilisers (e.g. gluconate, phosphates or phosphonates). The pharmaceutical agent according to the invention occurs in the form of a solution or in freeze-dried form and, shortly before application a solution of Tc-99m pertechnetate eluted from commercially obtained generators, or a perrhenate solution is added.

When used in vivo in nuclear medicine, the agents according to the invention are applied in quantities of $1.10^{-5}$ to $5.10^4$ nmol/kg body weight, preferably in quantities between $1.10^{-3}$ and $5.10^2$ nmol/kg body weight. Assuming an average body weight of 70 kg, the amount of radioactivity for diagnostic applications is between 0.05 and 50 mCi, preferably 5 to 30 mCi per application. The amount used for therapeutic applications is between 5 and 500 mCi, preferably 10–350 mCi. Application is normally by intravenous, intra-arterial or peritoneal or intra-tumoral injection of 0.1 to 2 ml of a solution of the agents according to the invention. Intravenous application is preferred.

The following examples illustrate the inventive idea in detail.

EXAMPLE 1

2-Methyl-2-(4-nitrobenzyl)-malonic acid dimethyl ester [1]

11.5 g (0.5 mol) of sodium in a stream of nitrogen was placed in a dry 1000 ml three-necked flask with a reflux condenser, a drying tube and a dropping funnel with pressure compensation. Next, 350 ml of methanol was carefully added dropwise and agitated until the sodium had completely dissolved. A methanolic solution of 87 g (0.5 mol) methylmalonic acid diethyl ester was added very slowly dropwise to the sodium methanolate solution, which was still warm. At the end of the addition, the mixture was stirred for a further 30 minutes, after which 4-nitrobenzyl bromide was added in portions, using a powder funnel. After everything had dissolved, the mixture was first reflux-heated for two hours and then agitated at room temperature overnight. The solvent was removed in a rotary evaporator and water was added to the residue, which was repeatedly extracted with ethyl acetate (250 ml portions). The combined organic extracts were washed with saturated common salt solution and dried over sodium sulphate. After removing the solvent, faintly yellow crystals were left. Recrystallisation was from dimethyl formamide (DMF) and water.

Melting point: 94.5°–95.0° C.
Yield: 74%
$^1$H-NMR-Data in DMSO/TMS 1.4 ppm (s,3H,Me); 3.5 ppm (s,2H,$CH_2Ar$); 3.8 ppm (s,6H,MeOOC); 7.2 ppm (d,2H,ArH); 8.2 ppm (d,2H,ArH)

2-Methyl-2-(4-nitrobenzyl)-malonic acid diamide [2]

5.0 g of the ester [1] was weighed in a 500 ml round-bottomed flask and dissolved in 200 ml methanol. Ammonia was introduced into the methanolic solution until saturation, after which the catalytic quantity of sodium was added and, at the end of evolution of gas, the flask was closed by a suction member with an air balloon and left at room temperature for at least one week. A white precipitate formed after a few days. After the entire educt had reacted (DC check) the precipitate was suction-filtered and the remaining solution was cooled to −20° C. in a deep freezer and suction-filtered again. The mother liquor was additionally concentrated in a rotary evaporator and the precipitate was again suction-filtered. The combined crystal fractions were recrystallised from acetonitrile. The white crystalline product was dried in a vacuum exsiccator.

Melting point: 179° C.
Yield: 91%
$^1$H-NMR-data in DMSO/TMS 1.22 ppm (s,3H,Me); 3.3 ppm (s,2H,CH$_2$Ar); 7.1 ppm (s(br),4H,CONH$_2$); 7.3 ppm (d,2H,ArH); 8.1 ppm (d,2H,ArH)

2-Methyl-2-(4-nitrobenzyl)-1.3-propane diamine [3]

The diamide [2] (5.0 g) was suspended, with exclusion of atmospheric humidity, in 25 ml abs. tetrahydrofuran in a 250-ml two-necked flask with reflux condenser, a drying tube and a septum. The flask was cooled in an ice bath, after which a solution of borane in THF was added through the septum using a 20 or 50-ml disposable syringe. After the required quantity of borane solution (80 ml of a 1M solution in THF) had been added, the mixture was heated to room temperature. After 30 minutes the mixture was reflux-boiled for 4 hours. After cooling to room temperature the excess of borane was carefully hydrolysed with water (a total of 16 ml water). At the end of gas evolution, the reaction mixture was quantitatively transferred to a 500-ml round-bottomed flask and the solvent was carefully drawn off in a rotary evaporator, leaving a white precipitate. 125 ml of 6N HCl was added to the precipitate, which was reflux-boiled for 3 hours. Next, the hydrochloric acid was slowly removed in a rotary evaporator. The residue ws absorbed in the minimum amount of water (about 50 to 70 ml) and placed in a prepared ion-exchange column (highly basic) and the pure amine was eluted with distilled water. The free diamine was collected (pH check) and the combined fractions were concentrated in the rotary evaporator. The residue was a faintly yellow oil.

Melting point (hydrochloride): 270° C.
Yield: 80%
$^1$H-NMR-Data in DMSO/TMS 1.0 ppm (s,3H,Me); 2.9 ppm (m,4H,CH$_2$NH$_2$); 3.0 ppm (s,2H,CH$_2$Ar); 7.5 ppm (d,2H,ArH); 8.2 ppm (d,2H,ArH); 8.5 ppm (s(br),4H,NH$_2$)

2-Methyl-2-(4'-nitrobenzyl)-N,N'-propylene-bis(-salicylidene-imine) [4]

A solution of 5.5 g salicylic aldehyde in 75 ml absolute ethanol was added dropwise with agitation to a solution of 5.6 g diamine [3] in 75 ml absolute ethanol. The colour of the resulting solution slowly changed to intense yellow. It was agitated for a further 3 hours at room temperature, during which time a yellow precipitate formed and was filtered after to −20° C. A total of 7.5 g of the diimine was obtained.

Melting point: 103° C.
Yield: 77%
$^1$H-NMR-data in CDCl$_3$/TMS 1.1 ppm (s,3H,Me); 3.0 ppm (s,2H,CH$_2$Ar); 3.5 ppm (m,4H,CH$_2$N=C); 6.9 ppm (m,4H,ArH); 7.3-7.4 ppm (m,8H,ArH); 8.2 ppm (d,2H,ArH); 8.4 ppm (s,2H,CH=N)

2-Methyl-2-(4'-nitrobenzyl)-N,N'-propylene-bis(salicyclidene amine) [5]

300 mg of sodium boron hydride was added with agitation to a solution of 2 g diimine [4] in 50 ml ethanol and agitated at 0° C. for two hours. Next, 20 ml water was added dropwise and agitated at room temperature for one hour, after which the solvent was removed in the rotary evaporator and the residue was dissolved in water. The mixture was brought to pH 11 with saturated potassium carbonate solution and the precipitate was dissolved in chloroform. After drying over sodium sulphate and removing the solvent, a crystalline residue was left. White crystals were recrystallised from acetonitrile.

Melting point: 151° C.
Yield: 81%
$^1$H-NMR-data in CDCl$_3$/TMS 0.9 ppm (s,3H,Me); 2.5 ppm (m,4H,CH$_2$NH); 2.8 ppm (s,2H,CH$_2$Ar); 3.9 ppm (m,4H,ArCH$_2$NH); 6.8 ppm (m,4H,ArH); 7.0-7.3 ppm (m,6H,ArH); 8.2 ppm (d,2H,ArH)

2-Methyl-2-(4'-aminobenzyl)-N,N'-propylene-bis(-salicylidene-amine) [6]

20 mg of 10% Pd/C in 25 ml of MeOH were suspended in a 50-ml two-necked flask and saturated with hydrogen. Next, the solution of 218 mg [5] (0.5 mmol) in 4 ml methanol and 833 μl of 6N hydrochloric acid was added through a septum, using a 5-ml disposable syringe. After the hydrogen had been absorbed, the catalyst was separated and the solvent was removed in vacuo, leaving white crystals, which were recrystallised from methanol.

Yield: 73%
$^1$H-NMR-data in DMSO/TMS 1.0 ppm (s,3H,Me); 2.5 ppm (m,4:H,CH$_2$NH); 2.8 ppm (s,2H,CH$_2$Ar); 4.1 ppm (m,4H,ArCH$_2$NH); 6.8-7.5 ppm (m,12H,ArH)

2-Methyl-2-(4-isothiocyanatobenzyl)-N,N'-propylene-bis-(salicylideneamine) [7]

An 85% solution of thiophosgene in carbon tetrachloride (0.2 ml, 2.23 mmol) was added to a solution of compound [6] (0.16 mmol) in 4 ml hydrochloric acid (3M). The reaction mixture was agitated at room temperature for 6 hours and then concentrated to dryness in vacuo.

Yield: 87%
$^1$H-NMR-data in DMSO/TMS 1.0 ppm (s,3H,Me); 2.8 ppm (m,4H,CH$_2$NH); 3.0 ppm (s,2H,CH$_2$Ar); 4.1 ppm (m,4H,ArCH$_2$NH); 6.8-7.4 ppm (m,12H,ArH)

EXAMPLE 2

2-(4-Nitrobenzyl)-malonic acid diethyl ester [8]

21.4 g of lithium diisopropyl amide was added to 210 ml anhydrous tetrahydrofuran in a stream of nitrogen in a dry 3-necked flask with a drying tube and dropping funnel with pressure compensation. Next, 58.0 g of malonic acid diethyl ester in 100 ml anhydrous tetrahydrofuran was added dropwise at room temperature in 40 minutes. After 30 minutes the reaction solution was cooled to −62° C. and 39.1 g of 4-nitrobenzyl bromide in tetrahydrofuran was slowly added dropwise with vigorous agitation, followed by agitation for a further hour at −62° C., after which the precipitate was filtered cold. The filtrate was concentrated in a rotary evaporator, and the residue was dissolved in 300 ml ethanol at 65° C. and separated from the insoluble residue. 34.7 g of faintly yellowish crystals were obtained after cooling.

Melting point: 57°-58° C.
Yield: 65%
$^1$H-NMR-data in CDCl$_3$TMS 1.2 ppm (t,6H,CH$_2$CH$_3$); 3.3 ppm (d,2H,CH$_2$Ar); 3.6 ppm (t,1H,CH); 4.1 ppm (q,4H,C$\underline{H_2}$CH$_3$); 7.4 ppm (d,2H,ArH); 8.1 ppm (d,2H,Ar$\overline{H}$)

2-(4-Nitrobenzyl)-malonic acid diamide [9]

This compound was prepared in the same manner as compound [2].
Melting point: 225°–228° C.
Yield: 98%
$^1$H-NMR-data in DMSO/TMS 3.1 ppm (d,2H,CH$_2$Ar); 3.4 ppm (t,1H,CH); 7.1 ppm (s,4H,NH$_2$); 7.4 ppm (d,2H,ArH); 8.2 ppm (d,2H,ArH)

2-(4-Nitrobenzyl)-1.3-propane diamine [10]

This compound was prepared in the same manner as compound [3].
Melting point (hydrochloride): 273°–275° C.
$^1$H-NMR-data in D$_2$0 1..3 ppm (t,1H,CH); 3.1 ppm (d,4H,C$\underline{H_2}$NH$_2$); 3.2 ppm (d,2H,CH$_2$Ar); 7.5 ppm (d,2H,C$\underline{H}$,ArH); 8.2 ppm (d,2h,ArH)

2-(4′-Nitrobenzyl)-N,N′-propylene-bis (salicylidene imine) [11]

This compound was prepared in the same manner as compound [4].
Melting point: 75° C.
Yield: 68%
$^1$H-NMR-data in CDCl$_3$/TMS 1.5 ppm (m,1H,CH); 3.2 ppm (d,2H,CH$_2$Ar); 3.5 ppm (m,4H,CH$_2$N=C); 7.1 ppm (m,4H,ArH); 7.3–7.4 ppm (m,8H,ArH); 8.2 ppm (d,2H,ArH); 8.4 ppm (s,2H,CH=N)

2-(4′-Nitrobenzyl)-N,N′-propylene-bis-(salicylidene amine) [12]

This compound was prepared in the same manner as compound [5].
Yield: 90%
$^1$H-NMR-data in CDCl$_3$/TMS 1.6 ppm (m,1H,CH); 2.5 ppm (m,4H,CH$_2$NH); 2.8 ppm (d,2H,CH$_2$Ar); 3.9 ppm (m,4H,ArCH$_2$NH); 6.9 ppm (m,4H,ArH); 7.1–7.3 ppm (m,6H,ArH); 8.1 ppm (d,2H,ArH)

2-(4′-Aminobenzyl)-N,N′-propylene-bis(salicylidene amine) [13]

This compound was prepared in the same manner as compound [6].
Yield: 84%
$^1$H-NMR-data in DMSO/TMS 1.5 ppm (m,1H,CH);; 2.5 ppm (m,4H,CH$_2$NH$_2$); 2.7 ppm (t,2H,CH$_2$Ar); 4.1 ppm (m,4H,ArCH$_2$NH); 6.8–7.5 ppm (m,12H,ArH)

EXAMPLE 3

1.7-Bis(2.3-Dihydroxyphenyl)-4-(4′-nitrobenzyl)-2.6-diazahepta-1.6-diene [14]

This compound was prepared in the same manner as compound [4].
Yield: 76%
$^1$H-NMR-data in CDCl$_3$/TMS 1.5 ppm (m,1H,CH); 3.1 ppm (d,2H,CH$_2$Ar); 3.5 ppm, (m.4H.CH$_2$N=C); 6.8–7.0 ppm (m,8H,ArH); 7.4 ppm, (m,2H,ArH): 8.2 ppm (d,2H,ArH); 8.4 ppm (s,2H,CH=N)

1.7-Bis(2.3-Dihydroxyphenyl)-4-(4′-nitrobenzyl)-2.6-diazaheptane [15]

This compound was prepared in the same manner as compound [5].
Yield: 38%
$^1$H-NMR-data in CDCl$_3$/TMS 1.6 ppm (m,1H,CH); 2.5 ppm (m,4H,CH$_2$NH); 2.9 ppm (s,2H,CH$_2$Ar); 4.0 ppm (m,4H,ArCH$_2$NH); 6.5–7.3 ppm (m,8H,ArH); 8.2 ppm (d,2H,ArH)

1.7-Bis(2.3-dihydroxyphenyl)-4-4(4-aminobenzyl)-2.6-diazaheptane [16]

250 mg of the nitro compound [15] was dissolved in 30 ml of 50% methanol (pH 11) and hydrogenated at room temperature with 25 mg Pd/Alox. After separation of the catalyst and concentration, 60 mg of a crystalline solid was left.
Yield: 27%
$^1$H-NMR-data in DMSO/TMS 1.5 ppm (m,1H,CH); 2.5 ppm (m,4H,CH$_2$NH$_2$); 2.7 ppm (t,2H,CH$_2$Ar); 4.1 ppm (m,4H,ArCH$_2$NH); 6.6–7.5 ppm (m,12H,ArH)

EXAMPLE 4

2-[4′-(Tetrahydro-2-pyranyloxy)butyl]-malonic acid dimethyl ester [17]

7.9 g (0.3 mol) of sodium in a stream of nitrogen was placed in a 500-ml 3-necked flask with reflux condenser, drying tube and dropping funnel with pressure equalisation. Next, 250 ml of anhydrous methanol was carefully added dropwise and agitated until the sodium had completely dissolved. A methanolic solution of 95.4 g (0.58 mol) malonic acid diethyl ester was added very slowly dropwise to the still-warm sodium methanolate solution. At the end of the addition process, the mixture was reflux-boiled for a further hour, after which 0.5 mol of 1-chloro-4-tetrahydro-pyranyloxybutane was slowly added dropwise. The mixture was then reflux-boiled overnight.

The solvent was removed in a rotary evaporator and water was added to the residue, which was repeatedly extracted with ethyl acetate. The combined organic extracts were washed with saturated common-salt solution and dried over sodium suphate. After removal of the solvent, a colourless oil was left. 66.4 g of the substituted malonic ester were obtained after distillation in vacuo.
Boiling-point $_{1mml}$ 148° C.
Yield: 70%
$^1$H-NMR-data in CDCl$_3$/TMS 1.6–2 ppm (m,1,12H,CH$_2$); 3.5–3.7 ppm (m,5H,CH+OTHP); 3.7 ppm (s,6H,COOMe); 4.6 ppm (t,1H,OTHP)

2-[4′-(Tetrahydro-2-pyranyloxy)butyl]-malonic acid diamide [18]

40 g of the substituted malonic ester [17] were weighed in a 1000-ml round-bottomed flask and 700 ml methanol was added. The solution was cooled to −40° C. and ammonia gas was added till saturation, followed by a catalytic quantity of sodium and agitation at the same temperature for 4 hours. After heating to room temperature, the precipitate was suction-filtered and the remaining solution was cooled to −20° C. in a deep-freezer and again suction-filtered. The combined crystal fractions were recrystallised from acetonitrile.
Yield: 82%
$^1$H-NMR-data in DMSO/TMS 1.3–2.1 ppm (m,12H,CH$_2$); 3.1–4.0 ppm (m,5H,CH,OTHP); 4.5 ppm (t,1H,OTHP); 7.2 ppm (s(br),4H,CONH$_2$)

2-[4′-(Tetrahydro-2-pyranyloxy)butyl]-1.3-propane diamine [19]

6.8 g (0.18 mol) of lithium aluminium hydride were added with exclusion of moisture to 400 ml of absolute THF in a 1000-ml round-bottomed flask with reflux condenser and dropping funnel. Next, 15.5 g (0.06 mol)

of the substituted malonic acid amide [18] in 100 ml absolute THF was slowly added dropwise and reflux-heated for 4 hours, then cooled to 0° C. 8 ml of water was carefully added followed by 6 ml of 20% caustic soda solution and a further 30 ml of water. The mixture was filtered and the remaining precipitate was twice extracted by boiling with THF. The combined filtrates were washed with saturated common-salt solution and dried over sodium sulphate. The solvent was removed in the rotary evaporator and the residue was distilled in vacuo.

Yield: 70%

$^1$H-NMR-data in CDCl$_3$/TMS 1.2–1.8 ppm (m,13H,CH,CH$_2$); 2.7–3.1 ppm (m,4H,CH$_2$NH$_2$); 3.4–3.6 ppm (m,4H, OTHP); 4.5 ppm (t,1H,OTHP)

4-(4'-Tetrahydropyranyl oxybutyl)-N,N'-propylene-bis(salicylidene inime) [20]

This compound was prepared in the same manner as compound [4].

Yield: 70%

$^1$H-NMR-data in CDCl$_3$/TMS 1.2–1.9 ppm (m,13H,CH,CH$_2$,OTHP); 3.2–3.7 ppm (m,8H,CH$_2$N=C,OTHP); 4.5 ppm (t,1H,OTHP); 6.8–7.1 ppm (m,8H,ArH); 8.4 ppm (s,2H,CH=N)

4-(4'-Tetrahydropyranyl oxybutyl)-N,N'-propylene-bis(salicylidene imine) [21]

This compound was prepared in the same manner as compound [5].

Yield: 61%

$^1$H-NMR-data in CDCl$_3$/TMS 1.2–1.9 ppm (m,13H,CH,CH$_2$,OTHP); 2.7 ppm (m,4H,CH$_2$NH); 3.4–3.6 ppm (m,4H,OTHP,CH$_2$OR); 4.5 ppm (t,1H,OTHP); 6.5–7.3 ppm (m,8H, ArH)

EXAMPLE 5

2-Methyl-2-[4'-(tetrahydro-2-pyranyloxyl)butyl]-malonic acid dimethyl ester [22]

This compound was prepared in the same manner as compound [17].

Yield: 78%

$^1$H-NMR-data in CDCl$_3$/TMS 1.4 ppm (s,3H,Me); 1.2–2.0 ppm (m,12H,CH$_2$); 3.5–3.8 ppm (m,4H,OTHP); 3.7 ppm (s,6H,COOMe); 4.6 ppm (t,1H,OTHP)

2-Methyl-2-[4'-(tetrahydro-2-pyranyloxyl)butyl]-malonic acid dimethyl ester [23]

This compound was prepared in the same manner as compound [18].

Yield: 86%

$^1$H-NMR-data in DMSO/TMS 1.3 ppm (s,3H,Me); 1.2–2.0 ppm (m,12H,CH$_2$); 3.1–4.0 ppm (m,4H, OTHP); 4.5 ppm (t,1H,OTHP); 7.1 ppm (s(br),4H,CONH$_2$)

2-Methyl-2-[4'-(tetrahydro-2-pyranyloxy)butyl]-1,3-propane diamine [24]

This compound was prepared in the same manner as compound [19].

Yield: 64%

$^1$H-NMR-data in CDCl$_3$/TMS 0.9 ppm (s,3H,Me); 1.2–1.9 ppm (m,12H,CH$_2$); 2.7 ppm (m,4H,CH$_2$NH$_2$); 3.3–3.8 ppm (m,4H,OTHP); 4.5 ppm (t,1H,OTHP)

2-Methyl-2-(4-tetrahydropyranyloxybutyl)-N,N'-propylene-bis(salicylidene imine) [25]

This compound was prepared in the same manner as compound [4]

Yield: 77%

$^1$H-NMR-data in CDCl$_3$/TMS 1.0 ppm (s,3H,Me); 1.2–1.9 ppm (m,12H,OTHP+CH$_2$); 3.2–3.7 ppm (m,8H,OTHP=CH$_2$N=C); 4.5 ppm (t,1H,OTHP); 7.0 ppm (m,4H,ArH); 7.3–7.5 ppm (m,4H,ArH); 8.3 ppm (s,2H,CH=N)

2-Methyl-2-[4'-(tetrahydro-pyranyl oxylbutyl)-N-N'-propylene-bis(salicylidene amine) [26]

This compound was prepared in the same manner as compound [5]

Yield: 89%

$^1$H-NMR-data in DMSO/TMS 1.0 ppm (s,3H,Me); 1.2–1.8 ppm (m,12H,OTHP+CH$_2$); 2.8–3.1 ppm (m,4H, CH$_2$NH$_2$); 3.3–3.9 ppm (m,8H,OTHP+ArCH$_2$NH); 4.5 ppm (t,1H,OTHP); 7.0 ppm (m,4H,ArH); 7.3–7.5 ppm (m,4H,ArH)

Cu-2-methyl-2-(4-tetrahydropyranyl oxybutyl)-N,N'-propylene-bis(salicylidene amine) [27]

400 mg of copper acetate (2 mmol) in 20 ml methanol was added dropwise to a suspension of 913 mg [26] (2 mmol) in 50 ml methanol and agitated at room temperature. After removal of the solvent in the rotary evaporator and drying with a vacuum pump, an oily residue was left. A crystalline residue was left after re-crystallisation from pyridine/chloroform.

Yield: 76%

Cu-2-methyl-2-(4-hydroxybutyl)-N,N'-propylene-bis(salicylidene amine) [28]

A solution of 877 mg [27] (1.7 mmol) in 5 ml methanol was added dropwise to a solution of 0.3 ml concentrated sulphuric acid in 5 ml methanol and agitated at room temperature for 15 hours. After cooling to 0° C., the mixture was carefully neutralised with sodium carbonate, with agitation and cooling. After removing the solvent, the residue was extracted with ether, washed with saturated common salt solution and dried over sodium sulphate.

Yield: 68%

Cu-2-methyl-2-(4-formylbutyl)-N,N'-propylene-bis(salicylidene amine) [29]

4.32 g of [28] (10 mmol) dissolved in 20 ml dichloromethane was added in one go to an agitated suspension of 3.23 g PCC in 20 ml anhydrous dichloromethane and the mixture was agitated at room temperature for 2 hours. 50 ml anhydrous ether was added, the mixture was decanted, the black residue was washed three times, each time with 50 ml ether, and the combined ether solutions were filtered over silica gel. An oily residue was left after removal of the solvent.

Yield: 59%

EXAMPLE 6

2-Butyl-2-[4'-(tetrahydro-2-pyranyloxy)butyl]-malonic acid dimethyl ester [30]

This compound was prepared in the same manner as compound 17.

Yield: 69%

¹H-NMR-data in CDCl₃/TMS 0.9 ppm (t,3H,Me); 1.2-2 ppm (m,18H,CH₂); 3.3-3.9ppm (m,4H,OTHP); 3.7 ppm (s,6H,COOMe); 4.6 ppm (t,1H,OTHP)

2-Butyl-2-[4'-tetrahydro-2-pyranyloxy)butyl]-malonic acid diamide [31]

This compound was prepared in the same manner as compound [18].
Yield: 86%
¹H-NMR-data in DMSO/TMS 0.9 ppm (t,3H,Me); 1.3-2.2 ppm (m,18H,CH₂); 3.1-3.9 ppm (m,4H,OTHP); 4.5 ppm (t,1H,OTHP)

2-Butyl-2-[4'-(tetrahydro-2-pyranyloxy)butyl]-1.3-propane diamine [32]

This compound was prepared in the same manner as compound [19].
Yield: 70%
¹H-NMR-data in CDCl₃/TMS 0.9 ppm (t,3H,Me); 1.2-1.9 ppm (m,18H,CH₂); 2.5-2.9 ppm (m,4H,CH₂NH₂); 3.3-4.1 ppm (m,4H,OTHP); 4.6 ppm (t,1H,OTHP)

1.7-Bis(2'-Pyrrolyl)-2-butyl-2-[4'(tetrahydro-2-pyranyloxy)butyl]-2.6-diazahepta-1.6-diene [33]

This compound was prepared in the same manner as compound [4].
Yield: 74%
¹H-NMR-data in CDCl₃/TMS 0.9 ppm (t,3H,Me); 1.2-1.9 ppm (m,18H,CH₂); 3.3-4.1 ppm (m,8H,OTHP+CH₂N=C); 4.6 ppm (t,1H,OTHP); 6.2 ppm (m,2H,ArH); 6.4 ppm (m,2H,ArH); 6.8 ppm (m,2H,ArH); 8.0 ppm (s,2H,CH=N)

1.7-Bis(2'-Pyrrolyl)-2-butyl-2-[4'-tetrahydro-2-pyranyloxy)butyl]-2.6-diazaheptane [34]

This compound was prepared in the same manner as compound [5].
Yield: 71%
¹H-NMR-data in CDCl₃/TMS 0.9 ppm (t,3H,Me); 1.2-1.9 ppm (m,18H,CH₂); 2.4 ppm (m,4H,CH₂NH); 3.3-4.1 ppm (m,8H,OTHP+ArCH₂NH); 4.6 ppm (t,1H,OTHP); 6.1-6.6 ppm (m,6H,ArH)

EXAMPLE 7

2-Allyl-malonic acid diamide [35]

This compound was prepared in the same manner as compound [2].
Melting point: 168.5°-169° C.
Yield: 94%
¹H-NMR-data in DMSO/TMS 2.4 ppm (m,2H,CH₂CH=CH₂); 3.0 ppm (t,1H,CH): 5.0 ppm (m,2H,CH=CH₂); 5.7 ppm (m,1H,CH₂CH=CH₂); 7.0 ppm (s br,2H,CONH₂); 7.3 ppm (s br,2H,CONH₂)

2-Allyl-1,3-propane diamine [36]

A suspension of 3.12 g of diamide [35] in 50 ml anhydrous tetrahydrofuran was slowly added, cooled on ice, to a suspension of 1.52 g lithium aluminium hydride in 50 ml anhydrous tetrahydrofuran. The mixture was slowly cooled to room temperature and then heated with reflux for eight hours. After cooling to room temperature, 10 ml water was added dropwise followed by 10 ml of 10% potassium hydroxide solution and a further 10 ml water. Precipitated aluminium hydroxide was filtered off and was twice briefly extracted by boiling, each time with 50 ml tetrahydrofuran. The combined filtrates were washed with saturated common-salt solution and dried over sodium sulphate and the residue was distilled in vacuo after evaporating the solvent.
Yield: 65%
¹H-NMR-data in CDCl₃/TMS 1.9 ppm (m,1H,CH); 2.1 ppm (d,2H,CH₂CH=CH₂); 2.7 ppm (d,4H,CH₂NH); 5.1 ppm (m,2H,CH₂CH=CH₂); 5.8 ppm (m,1H,CH₂CH=CH₂)

2-Allyl-N,N'-propylene-bis(salicylidene imine) [37]

This compound was prepared in the same manner as compound [4].
Yield: 83%
¹H-NMR-data in CDCl₃/TMS 1.5 ppm(m,1H,CH); 2.2-2.4 ppm (m,2H,CH₂CH=CH₂); 3.5 ppm (m,4H,CH₂N=C); 4.9 ppm (m,2H,CH=CH₂); 5.6 ppm (m,1H,CH=CH₂); 6.8-7.1 ppm (m,8H,ArH); 8.4 ppm (s,2H,CH=N)

2-(3-Bromo-2-hydroxypropyl)-N,N'-propylene-bis(-salicylidene imine) [38]

1.78 g (10 mmol) of NBS was added to a solution of 3.22 g [37] (10 mmol) in 50 ml of 6:1 THF/water and agitated for two days at room temperature with exclusion of light. The mixture was poured in 250 ml of water and repeatedly extracted, each time with 50 ml acetic acid, dried, concentrated and the residue was re-crystallised from acetonitrile.
Yield: 32%
¹H-NMR-data in CDCl₃/TMS 1.5 ppm (m,3H,CH+CH₂CHOH); 3.5 ppm (m,4H,CH₂N=C); 3.8 ppm (d,2H,CH₂Br); 4.1 ppm (m,1H,CHOH); 6.9 ppm (m,4H,ArH); 7.3 ppm (m,4H,ArH); 8.4 ppm (s,2H,CH=N)

2-(2,3-Epoxypropyl)N,N'-propylene-bis(salicylidene imine) [39]

A solution of 7.6 g [38] (18 mmol) in 100 ml methanol was added to a solution of 5.4 g potassium carbonate in 15 ml water and agitated for one hour at room temperature. The mixture was filtered and concentrated and the residue was diluted with 30 ml water, extracted with chloroform, dried over sodium sulphate and concentrated.
Yield: 76%
¹H-NMR-data in CDCl₃/TMS 1.5 ppm (m,3H,CH+CH₂CHOR); 2.6 ppm (m,2H,epoxide); 3.1 ppm (m,1H,epoxide); 3.5 ppm (m,4H,CH₂N=C); 6.9 ppm (m,4H,ArH); 7.3 ppm(m,4H,ArH); 8.4 ppm (s,2H,CH=N)

2-[2-Hydroxy-3-(2-nitroimidazolyl)-propyl]-N,N'-propylene-bis(salicylidene imine) [40]

A mixture of 250 mg of 2-nitroimidazole (2.2 mmol), 475 g of 1.8-bis-(dimethylamino)-naphthalene (2.2 mmol) and 920 mg (2.2 mmol) of [39] in 5 ml DMSO was heated to 80° C. with agitation for twenty-four hours in a 10 ml round-bottomed flask. After cooling the mixture was diluted with 50 ml water, repeatedly extracted with ethyl acetate, then washed with dilute hydrochloric acid and water, dried over sodium sulphate and concentrated. The mixture was recrystallised from methanol/water.
Yield: 28%
¹H-NMR-data in CDCl₃/TMS 1.4-1.5 ppm (m,3H,CH+CH₂CHOH); 2.9 ppm (m,2H,CHOH—CH₂—NR₂); 3.5 ppm (m,4H,CH₂N=C); 4.0 ppm (m,1H,CHOH); 6.9–7.4 ppm (m,10H,ArH); 8.4 ppm (s,2H,CH=N)

2-[2-Hydroxy-3-(2-nitroimidazolyl)-propyl]-N,N''-propylene-bis(salicylidene amine) [41]

This compound was prepared in the same manner as compound [4].
Yield: 63%
$^1$H-NMR-data in CDCl$_3$/TMS 1.4–1.5 ppm (m,3H,CH+CH$_2$CHOH); 2.5 ppm (m,4H,CH$_2$NH); 2.8 ppm (m,2H,CHOH—CH$_2$—NR$_2$); 3.9–4.1 ppm (m,5H,CHOH+ArCH$_2$NH); 6.9–7.4 ppm (m,10H,ArH)

EXAMPLE 8

2-Allyl-2-methyl-malonic acid diethyl ester [42]

This compound was prepared in the same manner as compound [1]
Yield: 76%
Boiling point: 25$_{mbar}$ 106°–107° C.
$^1$H-NMR-data in CDCl$_3$/TMS 1.3 ppm(t,6H,COOCH$_2$CH$_3$); 1.4 ppm (s,3H,Me); 2.6 ppm (d,2H, CH$_2$CH=CH$_2$); 4.2 ppm (q,4H,COOCH$_2$CH$_3$) 5.0 ppm (d br,1H,CH$_2$CH=CH$_2$); 5.1 ppm (d br, 1H,CH$_2$CH=CH$_2$); 5.7 ppm (m,1H,CH$_2$CH=CH$_2$)

2-Allyl-2-methyl-malonic acid diamide [43]

This compound was prepared in the same manner as compound [2].
Yield: 89%
$^1$H-NMR-data in DMSO/TMS 1.3 ppm (s,3H,Me); 2.2 ppm (d,2H,CH$_2$CH=CH$_2$); 4.9 ppm (d br, 1H,CH$_2$CH=CH$_2$); 5.0 ppm (d br, 1H,CH$_2$CH=CH$_2$); 5.8 ppm (m,1H,CH$_2$CH=CH$_2$)

2-Allyl-2-methyl-1,3-propane diamine [44]

This compound was prepared in the same manner as compound [36].
Yield: 62%
$^1$H-NMR-data in CDCl$_3$/TMS 1.0 ppm (s,3H,Me); 2.2 ppm (D,2H,CH$_2$CH=CH$_2$); 2.5 ppm (m,4H,CH$_2$NH); 4.9 ppm (d br,1H,CH$_2$CH=CH$_2$); 5.0 ppm (d br,1H,CH$_2$CH=CH$_2$); 5.8 ppm (m,1H, CH$_2$CH=CH$_2$)

2-Allyl-2-methyl-N,N'-propylene-bis(salicylidene imine) [45]

This compound was prepared in the same manner as compound [4].
Yield: 76%
$^1$H-NMR-data in CDCl$_3$/TMS 1.0 ppm (s,3H,Me); 2.2 ppm (d,2H,CH$_2$CH=CH$_2$); 3.7 ppm (m,4H,CH$_2$N); 5.1 ppm (m,2H,CH$_2$CH=CH$_2$); 5.8 ppm (m,1H,CH$_2$CH=CH$_2$); 6.9–7.4 ppm (8H,ArH; 8.4 ppm (s,2H,CH=N); 13.5 ppm (s,2H,ArOH)

2-Allyl-2-methyl-N,N'-propylene-bis(salicylidene amine) [46]

This compound was prepared in the same manner as compound [5].
Yield: 73%
$^1$H-NMR-data in CDCl$_3$/TMS 1.1 ppm (s,3H,Me); 2.3 ppm (d,2H,CH$_2$CH=CH$_2$); 2.8 ppm (m,4H,CH$_2$NH); 4.1 ppm (m,4H,ArCH$_2$NH); 5.1 ppm (m,2H,CH$_2$CH=CH$_2$); 5.8 ppm (m,1H,CH$_2$CH=CH$_2$); 6.8–7.4 ppm (8H,ArH); 13.5 ppm (s,2H,ArOH)

EXAMPLE 9

1.7-Bis(2-hydroxynaphthyl)-4-methyl-4-(4-nitrobenzyl)-2.6,diazahepta-1.6-diene[47]

This compound was prepared in the same manner as compound [4].
Yield: 80%
$^1$H-NMR-data in CDCl$_3$/TMS 1.2 ppm (s,3H,Me); 3.0 ppm (s,2H,CH$_2$Ar); 3.8 ppm (m,4H,CH$_2$N=C); 7.0 ppm (d,2H,ArH); 7.3–7.4 ppm (m,6H,ArH); 7.6–7.9 ppm (m,6H,ArH); 8.3 ppm (d,2H,ArH); 8.9 ppm (s,2H,CH=N)

1.7-Bis(2-Hydroxynaphthyl)-4-methyl-4-(4-nitrobenzyl)-2.6-diazaheptane [48]

This compound was prepared in the same manner as compound [5].
Yield: 52%
$^1$H-NMR-data in CDCl$_3$/TMS 1.0 ppm (s,3H,Me); 2.6 ppm (m,4H,CH$_2$NH); 2.9 ppm (s,2H,CH$_2$Ar); 4.0 ppm (m,4H,ArCH$_2$NH); 6.9–7.4 ppm (m,8H,ArH); 7.6–7.9 ppm (m,6H,ArH); 8.3 ppm (d,2H,ArH)

1.7-Bis(2-hydroxynaphthyl)-4-methyl-4-(4-aminobenzyl)-2.6-diazaheptane [49]

This compound was prepared in the same manner as compound [6].
Yield: 72%
$^1$H-NMR data in CDCl$_3$/TMS 1.1 ppm (s,3H,Me); 2.6 ppm (m,4H,CH$_2$NH); 2.9 ppm (s,2H,CH$_2$Ar); 3.9 ppm (m,4H,ArCH$_2$NH); 6.9–7.4 ppm (m,8H,ArH); 7.6–7.9 ppm (m,6H,ArH); 8.3 ppm (d,2H,ArH)

EXAMPLE 10

1.7-Bis(2'-thienyl)-4-(4'-nitrobenzyl)-2.6-diaza-hepta-1.6-diene [50]

This compound was prepared in the same manner as compound [4]
Yield: 91%
$^1$H-NMR data in CDCl$_3$/TMS 1.4 ppm (m,1H,CH); 3.2 ppm (d,2H,CH$_2$Ar); 3.5 ppm (m,4H,CH$_2$N=C); 6.9 ppm (m,4H,ArH); 7.2–7.4 ppm (m,4H,ArH); 8.2 ppm (d,2H,ArH); 8.3 ppm (s,2H,CH=N)

1.7-Bis(2'-thienyl)-4-(4'-nitrobenzyl)-2.6-diaza-heptane [51]

This compound was prepared in the same manner as compound [5]
Yield: 76%
$^1$H-NMR data in CDCl$_3$/TMS 1.4 ppm (m,1H,CH); 2.5 ppm (m,4H,CH$_2$NH); 2.8 ppm (d,2H,CH$_2$Ar); 3.8 ppm (m,4H,ArCH$_2$NH); 6.7 ppm (m,2H,ArH); 6.8 ppm (m,4H,ArH) 7.4 pmm (m,2H,ArH); 8.2 ppm (d,2H,ArH)

1.7-Bis(2'-thienyl)-4-(4'-aminobenzyl)-2.6-diaza-heptane [52]

This compound was prepared in the same manner as compound [6]
Yield: 88%
$^1$H-NMR data in DMSO/TMS 1.2 ppm (m,1H,CH); 2.4–2.5 ppm (m,6H,CH$_2$NH+CH$_2$Ar); 3.8 ppm (m,4H,ArCH$_2$NH); 6.5–6.6 ppm (m,4H,ArH); 6.8–6.9 ppm (m,6H,ArH)

EXAMPLE 11

2-Methyl-2-(2-propinyl)-malonic acid dimethyl ester [53]

This compound was prepared in the same manner as compound [1]
Yield: 66%
1H-NMR-data in CDCl3/TMS 1.5 ppm (s,3H,Me); 2.0 ppm (t,1H,CCH); 2.8 ppm (m,2H,CH2); 3.8 ppm (s,6H,COOMe)

2-Methyl-2-(2-propinyl)-malonic acid diamide [54]

This compound was prepared in the same manner as compound [2]
Yield: 72%
1H-NMR-data in DMSO/TMS 1.5 ppm (s,3H,Me); 1.9 ppm (m,1H,CCH); 2.6 ppm (m,2H,CH2)

2-Methyl-2-(2-propinyl)-1.3-propane diamine [55]

This compound was prepared in the same manner as compound [36]
Yield: 57%
1H-NMR-data in CDCl3/TMS 1.5 ppm (s,3H,Me); 1.9 ppm (m,1H,CCH); 2.5 ppm (m,6 h, CH2C+CH2N)

2-Methyl-2-(propinyl)-N,N'-propylene-bis(salicylidene imine) [56]

This compound was prepared in the same manner as compound [4]
Yield: 77%
1H-NMR-data in CDCl3/TMS 1.5 ppm (s,3H,Me); 2.0 ppm (t,1H,CCH); 2.6 ppm (m,2H,CH2); 3.7 ppm (m,4H,CH2N); 6.9-7.4 ppm (m,8H,ArH); 8.3 ppm (s,2H, CH=N)

2-Methyl-2-(propinyl)-N,N'-propylene-bis(salicylidene amine) [57]

This compound was prepared in the same manner as compound [5]
Yield: 78%
1H-NMR-data in CDCl3/TMS 1.5 ppm (s,3H,Me); 2.0 ppm (t,1H,CCH); 2.6-2.8 ppm (m,6H,CH2CC+CH2NH); 4.0 ppm (m,4H,ArCH2NH); 6.9-7.4 ppm (m,8H,ArH)

EXAMPLE 11a

2-Methyl-2-(2-propinyl)-malonic acid [58]

23.7 g [53] (127 mmol) were dissolved in 200 ml methanol and a solution of 28.3 g (708 mmol) of NaOH in 50 ml water was slowly added dropwise. The mixture was heated to 50° C. in a water bath for two hours, the solvent was removed in a rotary evaporator and the residue was dissolved in water. The mixture was acidified with semi-concentrated hydrochloric acid and the free carboxcylic acid was exacted with chloroform, washed and dried.
Yield: 84%
1H-NMR-data in DMSO/TMS 1.4 ppm (s,3H,Me); 2.6 ppm (d,2H,CH2); 2.9 ppm (t,1H,CCH)

2-Methyl-2-(2-propinyl)-malonic acid dichloride [59]

A mixture of 3.40 g [58] and 8.9 g of thionyl chloride and one drop of DMF were heated to boiling with agitation and with exclusion of moisture. When all the gas had evolved, the excess of thionyl chloride was removed in vacuo at room temperature and the residue was distilled in vacuo.

Yield: 91%
Boiling point: 125° C./14 mm

N,N'-Bis(2-methoxybenzyl)-2-(propinyl)-malonic acid diamide [60]

4.69 g [59] (24.3 mmol) in 100 ml dichloromethane was carefully added dropwise to a mixture of 6.67 g of 2-methoxybenzyl amine (48.6 mmol) and 5.06 g of triethylamine (50 mmol) in 100 ml diochloromethane, with exclusion of moisture. The mixture was agitated at room temperature for a further three hours, then repeatedly extracted with chloroform after adding water. The organic phase was successively washed with 1N HCl, saturated potassium carbonate solution and water and dried over sodium sulphate.
Yield: 64%
1H-NMR-data in CDCl3/TMS 1.5 ppm (s,3H,Me); 2.0 ppm (t,1H,CCH); 2.8 ppm (d,2H,CH2CC); 3.8 ppm (s,6H,OMe); 4.4 ppm (d,4H,CH2NH); 6.9-7.3 ppm (m,8H,ArH)

N,N'-Bis(2-methoxybenzyl)-2-methyl-2-(propinyl)-1,3-propane diamine [61]

This compound was prepared in the same manner as compound [44].
1H-NMR-data in CDCl3/TMS 1.5 ppm (s,3H,Me); 2.0 ppm (t,1H,CCH); 2.6-2.8 ppm (m,6H,CH2CC+CH2NH); 3.8 ppm (s,6H,OMe); 4.2 ppm (m,4H,ArCH2NH); 6.9-7.3 ppm (m,8H,ArH)

2-Methyl-2-(propinyl)-N,N'-propylene-bis(salicylidene amine [57]

A solution of 338 mg [61] (1.0 mmol) in 15 ml dichloromethane was cooled to 0° C. in a nitrogen atmosphere with exclusion of moisture. 1.75 g (7.0 mmol) of boron tribromide in 20 ml dichloromethane was added dropwise and with agitation through a disposal syringe and the mixture was agitated at room temperature over night. The mixture was hydrolysed with water, made weakly alkaline with saturated potassium carbonate solution, extracted with dichloromethane and the organic extracts were washed with saturated common salt solution. A solid residue was left after removing the solvent.
Yield: 79%

EXAMPLE 12

6-(4'-Nitrobenzyl)-3,3,9,9-tetramethyl-4,8-diazaundecane-2,10-dione-dioxime [62]

3.9 g of diamine [10] was dissolved in 90 ml methanol and cooled to 0° C., after which 6.5 g of 2-chloro-2-methyl-3-nitrosobutane were added with agitation. After heating to room temperature the mixture was agitated for two hours, boiled with reflux for a further two hours, the solvent was removed and the remaining solid was dissolved in water. The mixture was neutralised with sodium hydrogen carbonate and concentrated and the remaining precipitate was re-crystallised from ethanol.
Melting point: 197°-198° C.
Yield: 27%
1H-NMR-data in DMSO/TMS 1.3 ppm (s,12H,MeCNH); 1.8 ppm (s,6H,MeC=N); 2.3 ppm (m,1H,CH); 2.5 ppm (m,4H,CH2NH); 2.8 ppm (d,2H,CH2Ar); 7.4 ppm (d,2H,ArH);8.2 ppm (d,2H,ArH); 10.8 ppm (s,2H,HON=C)

6-(4'Aminobenzyl)-3.3.9.9-tetramethyl-4.8-diazaundecane-2.10-dione-dioxime [63]

250 mg of the nitro compound [62] as dissolved in 30 ml of 50% methanol (pH 11) and hydrogenated at room temperature with 25 mg of Pd/Alox. 60 mg of a crystalline solid was left after removal of the catalyst and concentration.

Yield: 26%

$^1$H-NMR-data in $D_2O$ 1.2 ppm (s,12H, MeCNH); 1.7 ppm (s,6H,MeC=N); 1.9 ppm (m,1H,CH); 2.5 ppm (m,4H,$CH_2$NH); 2.4 ppm (d,2H,$CH_2$Ar); 6.5 ppm (d,2H,ArH); 6.9 ppm (d,2H,ArH)

Cu-6-(4'-aminobenzyl)-3.3.9.9-tetramethyl-4.8-diazaundecane-2.10-dione-dioxime [64]

This compound was prepared in the same manner as compound [27].

Yield: 45%

Cu-6-14'-(biotin carbamoyl)benzyl]-3.3.9.9-tetramethyl-4.8-diazaundecane-2.10-dione-dioxime [65]

680 mg of NHS biotin (2 mmol) was added with agitation to a solution of 439 mg [64] (1 mmol) in 10 ml DMSO and heated to 50° C. for three hours. After cooling to room temperature, the mixture was agitated for a further fifteen hours. The solvent was then removed in vacuo and the residue purified with MPLC (silica gel, dichloromethane/ethanol/concentrated ammonia 20:20:3).

Yield: 75%

6-[(Biotin carbamoyl) benzyl]-3,3,9,9-tetramethyl-4,8-diazaundecane-2,10-dione-dioxime [66]

500 mg of potassium cyanide was added to a solution of 600 mg [65] in 75 ml water at 40° C. and agitated for two hours. The mixture was then concentrated to about 10 ml and the residue was purified with MPLC (silica gel, acetonitrile/concentrated ammonia 40:3).

Yield: 41%

Tc-99m complex of [66]

$5.6 \times 10^{-3}$ mol potassium tartrate in 1 ml $H_2O$, $4.8 \times 10^{-5}$ mol tin chloride in 1 ml $H_2O$ and 5 mCi of Tc-99m-pertechnetate were added to a solution of $1.86 \times 10^{-5}$ mol [62] in 1 ml EtOH/$H_2O$ 4:6 and incubated for ten minutes. The corresponding technetium complex was obtained with more than 90% purity.

EXAMPLE 13

6-(4'-Isothiocyanatobenzyl)-3,3,9,9-tetramethyl-4,8-diazaundecane-2,10-dione-dioxime [67]

This compound was prepared in the same manner as compound [7].

$^1$H-NMR-data in $D_2O$ 1.2 ppm (s,12H,MeCNH); 1.7 ppm (s,6H,MeC=N); 1.9 ppm (m,1H,CH); 2,6 ppm (m,4H,$CH_2$NH); 2.4 ppm (d,2H,$CH_2$Ar); 6.7 ppm (d,2H,ArH);7.2 ppm (d,2H,ArH)

EXAMPLE 14

2-Methyl-2-[44-(biotin carbamoyl)benzyl]-N,N'-propylene-bis(salicylidene amine) [68]

100 mg of the hydrochloride of aniline [6] (0.194 mmol) was dissolved in 10 ml water in a 5 ml round-bottomed flask at room temperature, and a freshly-prepared solution of 66.3 mg of biotin-NHS (0.194 mmol) in 1 ml dimethyl formamide was added, followed by 80 µl triethylamine with agitation. After fifteen hours the reaction mixture was concentrated in vacuo and the residue was dissolved in dimethoxyethane. Purification was brought about by HPLC. Column:M&W 250×4.6 mm, nucleosil 100 C-18.5 µm; developer ([acetonitrile]/[0.05M $KH_2PO_4$, pH 4.8])50:50 (v/v); flow rate: 1.0 ml/min UV detector 280 nm.

$^1$H-NMR -data in DMSO 1.1 ppm (s,3H,Me); 1.5–1.6 ppm (m,6H,$CH_2$); 2.5–2.8 ppm (m,8H,$CH_2$S,$CH_2$NH,$CH_2$CO); 2.9 ppm (s,2H,$CH_2$Ar); 3.1 ppm (M,1H,CHS); 4.0–4.3 ppm (m,6H,Ar$CH_2$NH,biotin-H); 6.4 ppm (s,2H,NH); 6.8–7.8 ppm (m,12H,ArH)

Tc-99m complex of [68]

10 µl of saturated tin tartrate solution was added to 25 µg of compound [68] in 50 µl NaCl solution pH9, and 1 mCi of Tc-99m pertechnetate from an Mo99/Tc99m generator was added. The resulting reaction mixture was left to stand at room temperature for five minutes. The reaction mixture was investigated by thin-film chromatography, showing complete reduction of the pertechnetate, and complexing of the reduced technetium by the ligand.

Analysis of the Tc99m complex, HPLC

PRP-1 HPLC columns made by Messrs. Hamilton, 150×4.1 mm, 5 µm poly(styrene divinylbenzene) copolymer were used for the analysis.

Developer: (acetonitrile/[($KH_2PO_4$ pH 7 0.01M)+1% methanol]) 50:50 (v/v), flow rate 1.5 ml/min. Radioactivity was detected by using an HPLC radioactivity monitor LB506 C-1 made by Messrs. Berthold. The resulting radiochemical purity of the Tc-99m complex was greater than 92%.

EXAMPLE 15

N,N'-bis[2-(benzylthio)benzoyl]-2-methyl-2-(4-nitrobenzyl)-1,3-propane diamine [69]

6.0 g of S-benzylthiosalicylic acid chloride (22,8 mmol) in a solution of 100 ml benzene and 60 ml dichloromethane were slowly added dropwise during an hour to a solution of 49 ml 1N NaOH (49 mmol) and a solution of 2.59 g [31] (11.6 mmol) in 100 ml benzene. The solution was then cooled to 0° C., water was added and the aqueous phase was repeatedly extracted with dichloromethane and dried over sodium sulphate. After removing the solvent, a yellow oil was left.

Yield: 77%

$^1$H-NMR-data in $CDCl_3$/TMS 1.0 ppm (s,3H,Me); 3.0 ppm (s,2H,$CH_2$Ar); 3.5 ppm (m,4H,NH$CH_2$); 4.1 ppm (s,4H,S$CH_2$Ar); 6.7 ppm (t,2H,CONH); 7.1–7.6 ppm (m,20H,ArH), 8.2 ppm (d,2H,ArH)

N,N'-bis[2-(benzylthio)benzyl]-2-methyl-2-(4-nitrobenzyl)-1.3-propane diamine [70]

27.6 ml of a 1M borane solution in THF was added dropwise to a solution of 2,98 g [69] (4.6 mmol) in 10 ml THF at 0° C., reflux-heated for two hours, cooled and 10 ml of a 1:1 mixture of HCl in water was added and the solvlent was removed in a rotary evaporator. After neutralising with 1N NaOH the mixture was extracted with dichloromethane, and dried over sodium sulphate and the solvent was removed, leaving a faintly yellow oil.

Yield: 58%

¹H-NMR-data in CDCl₃/TMS 1.0 ppm (s,3H,Me); 2.9 ppm (s,2H,CH₂Ar); 3.1 ppm (m,4H,NHCH₂); 3.3 ppm (m,4H,ArCH₂NH); 4.1 ppm (s,4H,SCH₂Ar); 7.1-7.6 ppm (m,20H,ArH), 8.2 ppm (d,2H,ArH)

N,N'-bis(2-mercaptobenzyl)-2-methyl-2-(4-nitrobenzyl)-1.3-propane diamine [71]

Sodium was added to a solution of 1.24 g [70] (2.0 mmol) in 30 ml liquid ammonia until the colour became permanently blue. After thirty minutes the excess sodium was destroyed by adding ammonium chloride. After the ammonia evaporated, the residue was dissolved in water and extracted with chloroform. After drying and removal of the solvent, a white residue was left.

Yield: 69%

¹H-NMR-data in CDCl₃/TMS 1.1 ppm (s,3H,Me); 2.9 ppm (s,2H,CH₂Ar); 3.0 ppm (m,4H,NHCH₂); 3.3 ppm (m,4H,ArCH₂NH); 6.9-7.4 ppm (m,10H,ArH),8.2 ppm (d,2H,ArH)

EXAMPLE 16

N,N'-bis[2-(benzylthio)benzoyl]-2-[4'(phenoxy)butyl]-1.3-propane diamine [72]

6.0 g of S-benzylthiosalicylic acid chloride (22.8 mmol) in a solution of 100 ml benzene and 60 ml dichloromethane was added slowly dropwise during an hour to a solution of 49 ml of 1N NaOH (49 mmol) and a solution of 2.34 g of 2-(4'-phenoxy)butyl-1,3-propane diamine (11.6 mmol) in 100 ml benzene. The solution was then cooled to 0° C., water was added, and the aqueous phase was repeatedly extracted with dichloromethane and dried over sodium sulphate. After removal of the solvent, a yellow oil was left.

Yield: 68%

¹H-NMR-data in CDCl₃/TMS 1.2-1.8 ppm (m,7H,CH,CH₂); 3.5 ppm (m,4H,NHCH₂); 4.1 ppm (s,4H,SCH₂Ar); 4.3 ppm (t,2H,CH₂OAr); 6.7 ppm (t,2H,CONH); 7.1-7.8 ppm (m,23H,ArH)

N,N'-bis[2-(benzylthio)benzyl]-2-[4'(phenoxy)butyl]-1.3-propane diamine [73]

This compound was prepared in the same manner as compound [70]

Yield: 58%

¹H-NMR-data in CDCl₃/TMS 1.2-1.8 ppm (m,7H,CH,CH₂); 3.3 ppm (m,4H,ArCH₂NH); 3.5 ppm (m,4H,NHCH₂); 4.1 ppm (s,4H,SCH₂Ar); 4.3 ppm (t,2H,CH₂OAr); 7.1-7.8 ppm (m,23H,ArH)

N,N'-bis[2-(benzylthio)benzyl]-2-[4-bromobutyl]-1.3-propane diamine [74]

A solution of 1.29 g [73] (2 mmol) in 50 ml glacial acetic acid/48% HBr (80:20 v/v) was heated to 95° C. in an argon atmosphere for four days. After removal of the solvent, a solid residue was left.

Yield: 69%

¹H-NMR-data in DMSO/TMS 1.2-1.8 ppm (m,7H,CH,CH₂); 3.3 ppm (m,4H,ArCH₂NH); 3.4-3.6 ppm (m,6H,CH₂OBr,NHCH₂); 4.1 ppm (s,4H,SCH₂Ar); 7.1-7.8 ppm (m,23H,ArH)

N,N'-bis[2-(benzylthio)benzyl]-4-[5'-aminomethyl)-(6-amino)hexanoxylbenzoic acid [75]

A solution of 8.31 g of 4-hydroxybenzoic acid ethyl ester (50 mmol) in 25 ml DMF was slowly added dropwise to a suspension of 1.2 g of sodium hydride (50 mmol) in 25 ml DMF, and agitated for a further thirty minutes. Next, a solution of 31.6 g [74] in 75 ml DMF was carefully added dropwise and heated to 80° C. for six hours. After cooling to room temperature, the mixture was diluted with ice water, the alkaline solution was weakly acidified and repeatedly extracted with dichloromethane, and after drying the solvent was removed, leaving a solid residue.

Yield: 64%

¹H-NMR-data in DMSO/TMS 1.2-1.8 ppm (m,7H,CH,CH₂); 3.3 ppm (m,4H,ArCH₂NH); 3.5 ppm (m,4H,NHCH₂); 4.1 ppm (s,4H,SCH₂Ar); 4.3 ppm (t,2H,CH₂OAr); 7.1-8.2 ppm (m,22H,ArH)

N,N'-bis[2-(mercaptobenzyl)-4-[5'-aminoethyl)-(6'-amino)hexanoxy]benzoic acid [76]

This compound was prepared in the same manner as compound [73]

Yield: 73%

¹H-NMR-data in DMSO/TMS 1.2-1.8 ppm (m,7H,CH,CH₂); 3.3 ppm (m,4H,ArCH₂NH); 3.5 ppm (m,4H,NHCH₂); 4.3 ppm (t,2H,CH₂OAr); 7.1-8.3 ppm (m,12H,ArH)

N,N'-bis[2(mercaptobenzyl)-4-[(5'-aminoethyl)-(6'-amino)hexanoxy]benzoic acid 2,3,5,6-tetrafluorophenylester [77]

A solution of 1.04 g of 1-(3-dimethyl aminopropyl)-3-ethyl carbodiimide (5.5 mmol) in 20 ml acetonitrile was added dropwise in 5 minutes to a solution, cooled to 0° C., of 2.47 g of carboxylic acid [76] (5 mmol) and 830 mg 2,3,5,6-tetrafluorophenol (5 mmol) in 20 ml acetonitrile, and heated to 60° C. for 4 hours. 25 μl acetic acid was added followed by agitation for a further hour, filtration and extraction of the residue twice with hot acetonitrile. The combined filtrates were concentrated to dryness and the residue was recrystallised.

Yield: 55%

¹H-NMR-data in CDC₃₃/TMS 1.1-1.9 ppm (m,7H,CH,CH₂); 3.2 ppm (m,4H,ArCH₂NH); 3.5 ppm (m,4H,NHCH₂); 4.1 ppm (t,2H,CH₂OAr); 7.1-8.3 ppm (m,13H, ArH)

EXAMPLE 17

Tc-99m-complex of [7]

A solution of 5.0 mg [6] in water was brought to pH 11 with 0.1N NaOH, after which 1 ml of EtOH was added and the solution was made up to 10 ml with water. 400 μl of the solution with 80 μl of saturated tin tartrate solution and 8 mCl of Tc-99m pertechnetate from an Mo99/Tc99m generator was added and left to stand five minutes. The solution was then washed three times, each time with 2 ml chloroform, the organic phase was dried over a short sodium sulphate column, 50 μl of thiophosgene was added and the mixture was incubated at room temperature for 5 minutes. 100 μl of isopropanol was then added, the chloroform was evaporated with argon, and 900 μl of a 1% PVP solution in water was added to the residue.

EXAMPLE 18

Labelling an Isothiocyanate-Containing Chelating Agent and Coupling it to Proteins The process of coupling isothiocyanate-containing Tc-chelating agents [compound 7] to proteins will be described, using F(ab)2 fragments of the monoclonalen antibody 17-1A as an example. Any other protein or substance containing an amino group can be used instead of the antibody fragments.

The monoclonal antibody 17-1A was obtained by methods known in the literature, after application of $10^7$ of the corresponding hybridoma cells to the abdominal cavity of a Balb/c-mouse and suction of the ascites fluid after 7–10 days. Purification was brough about likewise by methods known in the literature, by ammonium sulphate precipitation and affinity chromatography over protein A-sepharose. The purified antibody (10 mg/ml) was treated with 25 µg/ml pepsin at pH 3.5 for 2 hours and then isolated by FPLC. Before coupling to the chelating agent, the fragments were dialysed against 0.1M $KH_2PO_4$/0.1M $NaHCO_3$, pH 8.5, at 4° C. for 12–24 hours. The protein concentration was adjusted to 10 mg/ml. A 5-fold molar excess of the NCS-containing chelating agent [Example 1] was dissolved in a minimum amount of the same buffer and added to the protein solution. In order to form the conjugate, the mixture was incubated at 37° C. for 3 hours. Next, the conjugate was dialysed 24–48 hours against PBS (phosphate-buffered saline) with repeated change of buffer, and the protein concentration was re-adjusted to 10 mg/ml when necessary. Before labelling with Tc-99m, the conjugate could be kept in acid-cleaned glass vessels after sterile filtration at 4° C.

1 mg of the antibody fragment coupled to the chelating agent [7] was labelled with TC-99m by adding 10 mCi pertechnetate solution (=1–2 ml) and 100 µg tin-II chloride in a solution of Na pyrophosphate (1 mg/ml) scavenged with argon or by ligand exchange e.g. by mixing the solution with a commercially obtainable glucoheptonate kit to which pertechnetate had been added.

EXAMPLE 19

Coupling an isthiocyanate-containing Tc-99m complex to proteins

Alternatively, coupling to the antibody fragments can be brought about after complexing the chelating agents with Tc-99m. The monoclonal antibody 17-1A was obtained as described in Example 17. As in Example 17, purification was brought about by ammonium sulphate precipitation and affinity chromatography over protein A-sepharose. The purified antibody (10 mg/ml) was treated with 25 µl/ml pepsin at pH 3.5 for 2 hours and then isolated by FPLC. Before coupling with the chelating agents, the fragments were dialysed against 0.1M $KH_2PO_4$/0.1M $NaHCO_3$, pH 8.5, at 4° C. for 12–24 hours. The protein concentration was adjusted to 10 mg/ml.

The Tc-99m complex, prepared as in Example 16, was added in a molar ratio of 1:10 (complex:protein) to the protein solution. To form the conjugate, the mixture was incubated at 37° C. for an hour. The distribution among organs in hairless mice was carried out as in Example 19 and gave similar results.

EXAMPLE 20

Bio-distribution of a Protein-bonded Tc-99M Complex

The bio-distribution of protein-bonded chelates will be described, using a conjugate of F(ab)2 fragments of the monoclonal antibody 17-1A and the compound [7] prepared in Example 1 as a model. The antibody from which the fragments were obtained recognise an antigen expressed from the human carcinoma cell line "HT-29". A control cell line likewise obtained from a human carcinoma (MX-1) did not express this antigen. Isolated cells from both lines were subcutaneously administered to immune-deficient hairless mice. After the tumours had grown to a size of 300–800 mg, the mice were intravenously given 20 µg of the chelate conjugate [Example 17] labelled with 200 µCi. The conjugates were first freed from low-molecular constituents by gel filtration on PD 10 columns manufactured by Messrs. Bio-Rad. The immune reactivity of the conjugates was 70–80% as determined by bonding to an excess of antigen in the cell. The bio-distribution 24 hours after administration of the conjugate was determined by killing the animals, removing the organs and measuring the radioactivity therein. The following Table gives the measured amounts of radioactivity and shows a marked concentration of the chelate in the antigen-positive tumour.

| Organ | % of applied dose per gram of tissue |
| --- | --- |
| Spleen | 0.3 |
| Liver | 1.2 |
| Kidneys | 2.8 |
| Lung | 0.8 |
| Muscle | 0.1 |
| Blood | 0.6 |
| MX-1 | 1.8 |
| HT29 | 12.1 |

EXAMPLE 21

Bio-distribution of a Biotin-containing Chelate

20 µl of a commercially obtainable streptavidin-coupled sepharose-gel (corresponding to 20 µg streptavidin) was administered to the left hind-leg muscle of a rat weighing 200 g. About 30 minutes afterwards 5 µg of the compound prepared in Example 12, labelled with 200 µCi of Tc-99m, was administered intravenously. The radioactivity in the individual organs of the rat was measured after 4 hours. A 14-fold increase in radioactivity in the left hind-leg muscle in comparison with the right hind-leg muscle showed a marked specific Concentration of the Tc complex through bonding to streptavidin sepharose. No activity above 1% of the applied dose per gram of tissue was detected in any other organ.

The maximum concentration, apart from the left hind-leg muscle (1.4% of the administered dose per gram of tissue) occurred in the kidneys (0.6% of the administered dose per gram of tissue). About 93% of the administered radioactivity was found in the urine after 4 hours.

EXAMPLE 22

Bonding the Tc-99 complex prepared in Example 7 to hypoxic cell aggregates

Bonding of the misonidazole derivative labelled with Tc was demonstrated in vitro on cells of Morris Hepatom 7777. These cells have the property of growing in the form of spheroids or large floating cell aggregates and are thus more like a tumour than individual cells. For the purpose of the incubation in various concentrations of oxygen, the cells were sown in 60-mm culture dishes, which were placed in a gas-tight closable glass vessel heated to 37° C. The vessel was vigorously scavenged for 30 minutes with a mixture of $N_2$, 5% $CO_2$ and 0% to 10% $O_2$. Next, 50 μmol/l of the compound [Example 7] labelled with 50 μCi of Tc-99 m was added through a silicone membrane, using an injection cannula, and throughly mixed. After an hour the vessel was opened, the cell aggregate was separated from the nutrient medium by centrifuging and washed once with nutrient medium, and was incubated in the nutrient medium for a further hour without adding the compound [Example 7] and in a normal atmosphere with addition of 5% $CO_2$ at 37° C. The cells were then isolated and the radioactivity relative to the amount of protein was determined. It was found that for a given amount of protein, the amount of radioactivity was about 2.8 times higher in cells incubated without oxygen. This shows the concentration of the compound [Example 7] in hypoxic cells.

We claim:

1. A compound according to formula I

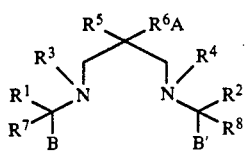

where $R^1$, $R^2$ and $R^5$ are the same or different and stand for hydrogen or a $C_{1-6}$-alkyl radical, substituted optionally by a hydroxyl group, $R^3$ and $R^4$ are the same or different and stand for a hydrogen atom or $C_{1-6}$-alkyl or amino($C_{1-6}$)-alkyl or carboxymethyl or ($C_{1-6}$-alkoxycarbonyl)methyl or ($C_{1-6}$-alkoxycarbonyl)benzyl radical, $R^6$ stands for a $C_{1-6}$-alkylene radical, $R^7$ and $R^8$ are the same or different and stand for hydrogen or a $C_{1-6}$-alkyl radical and B and B' are the same or different and stand for a phenyl or naphthyl or 2-mercaptophenyl or thienyl or pyrrolyl or nitrosomethyl radical, each radical substituted optionally with 1-3 hydroxyl groups, wherein the nitrosomethyl radical having the formula

where $R^x$ denotes a $C_{1-6}$-alkyl radical which, optionally together with $r^1$ or $R^2$, is cyclised via a trimethylene or tetramethylene group to form a 5 or 6 ring, and A denotes a functional group C, where C stands for an amino or hydrazino or hydrazido or carboxy or $C_{2-6}$-alkynyl or alkenyl or hydroxyl or aminophenyl of oxiranyl or fluorinated phenoxycarbonyl or halogen or formyl or nitrile or phenylisothiocyanate or a succinimide oxycarbonyl radical which latter is substituted optionally with a sodium sulphate radical, or contains a compound T, bonded by means of the functional group C, which selectively concentrates in lesions or certain tissues, where T stands for monoclonal antibodies or fragments thereof or hormones or enzymes or growth factors or ligands for cell membrane receptors or steroids or neurotransmitters or lipids or saccharides or amino acids or oligopeptides or biotin or radiosensitizers, and complexes thereof with radioactive metal ions suitable for diagnosis and tumor therapy, and salts thereof with inorganic and organic acids.

2. A compound according to claim 1, characterised in that $R^1$, $R^2$, $R^7$ and $R^8$ stand for hydrogen atoms or methyl radicals.

3. A compound according to claim 1, characterised in that the functional group C contained in A is a carboxy or amino or $C_{2-8}$-alkynyl or $C_{2-8}$-alkenyl or nitrile or tetrahydropyranyloxy or oxiranyl or aminophenyl or phenylisothiocyanate radical or a compound T.

4. A compound according to claim 3, wherein T is monoclonal antibodies, fragments thereof, biotin or misonidazole and bonded by means of C.

5. A compound according to claim 1, wherein the radiosensitizer is misonidazole.

6. A compound according to claim 1 which is a metal chelate containing at least one coordinate-bonded radioactive ion of Tc, Re, Cu, Co, Ga, Y or In.

7. A compound according to claim 6, wherein the coordinate-bonded radioactive ion is Tc or Re.

8. A pharmaceutical agent containing at least one chelate according to claim 1, optionally containing conventional galenic additives.

* * * * *